United States Patent [19]

Muller et al.

[11] 4,028,417

[45] June 7, 1977

[54] PROCESS FOR THE MANUFACTURE OF CYCLOHEXANDIONE-1,3

[75] Inventors: Werner Heinrich Müller, Aldersbach, Germany; Tomas Weil, Sao Paulo, Brazil

[73] Assignee: Hoechst Aktiengesellschaft, Frankfurt am Main, Germany

[22] Filed: July 28, 1976

[21] Appl. No.: 709,290

[30] Foreign Application Priority Data

July 30, 1975 Germany .......................... 2533919

[52] U.S. Cl. ........................................... 260/586 C
[51] Int. Cl.² ........................................ C07C 45/00
[58] Field of Search ................................ 260/586 C

[56] References Cited

UNITED STATES PATENTS

| | | | |
|---|---|---|---|
| 2,158,071 | 5/1939 | Hansley | 260/586 C |
| 2,218,026 | 10/1940 | Hansley | 260/586 C |
| 3,504,036 | 3/1970 | Schick et al. | 260/586 C |
| 3,922,307 | 11/1975 | Muller | 260/586 C |
| 3,932,511 | 1/1976 | Schaafsma et al. | 260/586 C |
| 3,950,438 | 4/1976 | Schaafsma et al. | 260/586 C |

OTHER PUBLICATIONS

Vorlander et al., "Amn.", vol. 294, pp. 270–271.
Bornstein et al., "C. A.", 48:9933e, (1954).
Kost et al., "Zhur. Absch. Khim", 32:3983–3986, (1962).
Mannich et al., "Ber", vol. 71, pp. 2090–2091, (1938).

*Primary Examiner*—Norman Morgenstern
*Attorney, Agent, or Firm*—Curtis, Morris & Safford

[57] ABSTRACT

Cyclohexanediones-1,3 are prepared in a good selectivity by reacting an α,β-unsaturate carboxylic acid ester with a ketone in the liquid phase in the presence of a strong base and a solvent selected from the group consisting of carboxylic acid amides, phosphoric acid amides, sulfoxides, sulfones, and glycol dialkyl ethers.

3 Claims, No Drawings

PROCESS FOR THE MANUFACTURE OF CYCLOHEXANDIONE-1,3

This invention relates to a one stage process for the manufacture of cyclohexanediones-1,3. Cyclohexanediones-1,3 can be transformed by dehydrogenation into industrially important resorcinols.

It has been proposed to prepare cyclohexanediones-1,3 by hydrogenation of resorcinols. This process has, however, the drawback that resorcinols are difficulty accessible and it is, therefore, desirable to proceed inversely, i.e. to use cyclohexanediones-1,3 as intermediates for the manufacture of resorcinols. In this manner there can also be prepared substituted resorcinols suitable as coupling components for dyestuffs and as antiseptics.

The cyclization of 4-oxocarboxylic acid alkyl esters to obtain cyclohexanediones-1,3 in the liquid phase (German Offenlegungsschrift DOS 2,245,270) or in the gaseous phase (German Offenlegungsschrift 2,412,313) is already disclosed. Both processes have the disadvantage that two stages are required.

5-Ketonitriles can be subjected to a cyclization in the presence of sulfuric or phosphoric acid whereby cyclohexanediones-1,3 are obtained (German Offenlegungsschrift 2,144,170). The use of high amounts of sulfuric acid or phosphoric acid and the necessity to operate in two separate reaction stages is, however, disadvantageous from an industrial point of view.

It has also been proposed to prepare 4-pentyl-cyclohexanedione-1,3 by a one-stage synthesis (cf. J. Org. Chem. 1957, page 1268) by reacting methylhexyl ketone and acrylic acid ethyl ester in the presence of sodium methylate in xylene. A considerable inconvenience of this process is the low selectivity of 27% which does not permit an economical production.

The present invention provides a process for the manufacture of a cyclohexanedione-1,3 of the formula

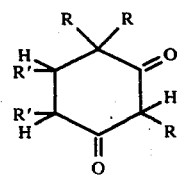

in which each of the radicals R, which may be identical or different, represents hydrogen, an alkyl group or an aryl group and the radicals R' represent hydrogen or an alkyl group, the cyclohexanedione-1,3 having up to 24 carbon atoms altogether, by reacting an $\alpha,\beta$-unsaturated carboxylic acid ester of the formula

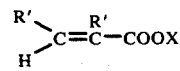

in which R' has the aforesaid meaning and X stands for an alkyl group, with a ketone of the formula

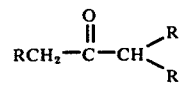

in which R has the aforesaid meaning, in the liquid phase and in the presence of a strong base and of a solvent, which comprises using a solvent belonging to one of the following classes of compounds:

a. carboxylic acid amides of the formulae

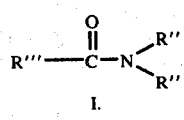 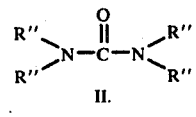

in which the radical R''' represents hydrogen or an alkyl group and each of the radicals R'', which may be identical or different, represents an alkyl group or an aryl group, or two radicals R'' bound to the same nitrogen atom or one radical R'' together with the radical R''' may form together a ring of methylene groups;

b. phosphoric acid amides of the formula

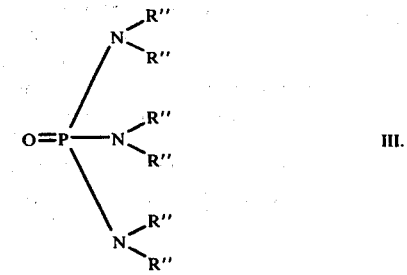

in which the radicals R'' have the same meaning as in formulae I and II;

c. sulfoxide and sulfones of the formulae

 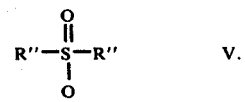

in which the radicals R'' have the same meaning as in formulae I and II; or d. ethers of the formula

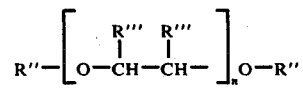

in which n is in the range of from 1 to 5 and the radicals R'' and R''' have the same meaning as in formulae I and II.

The substituents R and R' in the $\alpha,\beta$-unsaturated carboxylic acid esters and ketones used as starting compounds can represent alkyl groups or hydrogen and R can further represent an aryl group.

The alkyl groups can be linear, branched or cyclic and generally contain up to 12 carbon atoms. In the case of linear or branched radicals they may also be substituted by aryl groups such as phenyl or naphthyl. Especially suitable linear, branched or cyclic alkyl groups are methyl, ethyl, propyl, butyl, pentyl, hexyl, octyl, dodecyl, cyclohexyl, or cyclododecyl. The alkyl groups preferably contain up to 6 carbon atoms.

The aryl groups generally have up to 14 carbon atoms and may be substituted by alkyl groups having up to 6 carbon atoms, the phenyl and naphthyl radical being preferred.

Especially suitable ketones to be used as starting compounds are acetone, methylethyl ketone, methylpropyl ketone, methylisopropyl ketone, methylisobutyl ketone, diethyl ketone, methylbutyl ketone, methylpentyl ketone, methylhexyl ketone, methylheptyl ketone, methyloctyl ketone, cyclopentanone, cyclohexanone, 2-methylcyclohexanone and 4-methylcyclohexanone.

α,β-unsaturated carboxylic acid esters that are especially suitable are the methyl, ethyl, butyl, isopropyl, isobutyl and ethylhexyl esters of acrylic acid, methacrylic acid and crotonic acid.

As strong bases the alkali metal and alkaline earth metal alcoholates, oxides, amides and hydrides and the metals themselves can be used.

The radical R''' in the carboxylic acid amide of formula I can be hydrogen or an alkyl group. In all solvents claimed the radical R'' can stand for alkyl or aryl. The said alkyl and aryl groups R''' and R'' have the same meaning as the alkyl or aryl radicals R and R' in the starting compounds. In the claimed solvents of formulae I, II, III each time two of the radicals R'' at the same nitrogen atom and additionally in the carboxylic acid amide of formula I one radical R'' and the radical R''' may form a ring of methylene groups generally having up to 12 ring members, preferably up to 6 ring members. Compounds of this type are, for example

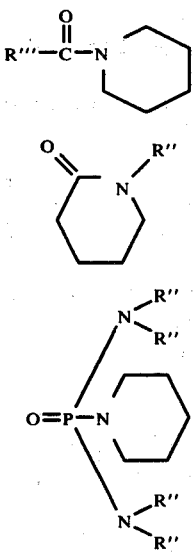

Especially suitable solvents are dimethyl formamide (DMF), dimethyl acetamide (DMAC), N-methyl-formanilide, N-methyl-pyrrolidone, tetramethyl urea, hexamethyl-phosphoric acid amide, dimethyl sulfoxide, sulfolane, dioxane, monoethylene glycol dimethyl ether (DME), diethylene glycol dimethyl ether (DEDME), diethylene glycol diethyl ether (DEG), ethylene glycol monomethyl ether, triethylene glycol dimethyl ether (TDM), pentaethylene glycol dimethyl ether (PDM), methyl glycol tert.butyl ether (MGT), ethyl glycol tert.butyl ether (AGT), butyl glycol tert.butyl ether (BGT), methyl diglycol tert.butyl ether (MDGT), ethyl diglycol tert.butyl ether (ADGT), butyl diglycol tert.butyl ether (BDGT), the cyclic polymer of ethylene oxide (EOCT).

The carboxylic acid amides, phosphoric acid amides, sulfoxides, sulfones and linear ethers can be used in admixture with solvents which are inert in the reaction.

The proportion of inert solvent may amount up to 50%, preferably up to 30%. Suitable inert solvents are, for example, methanol, ethanol, isopropanol, glycol, n-butanol, the ketone to be condensed, diethyl ether, diisopropyl ether, tetrahydrofurane, benzene, toluene, xylene, acetonitrile ethyl acetate and propanediol diacetate.

In general, the process of the invention is carried out at a temperature in the range of from −10° C to +150° C, preferably 0° to 100° C, at atmospheric pressure or under reduced pressure.

The solvent is generally used in an excess of from 2:1 to 1,000:1, calculated on the weight of ester.

The ratio of ketone to unsaturated ester is normally in the range of from 0.1:1 to 10:1.

According to a preferred embodiment of the process of the invention the mixture of ketone and ester is added dropwise, while intensely stirring, to the mixture of solvent and strong base. When the reaction is terminated, the reaction mixture is acidified to a pH of about 3–4, the salt formed as by-product is filtered off and the solvent is removed under reduced pressure. The crude product is then recrystallized, for example from the ethyl ether/acetic acid ethyl ester.

The following examples illustrate the invention.

COMPARATIVE EXAMPLE 1: (according to the method described in J. Org. Chem. (1957), page 1268)

40 Grams of ethyl acrylate were added to a suspension of 16.2 grams of sodium methylate in 200 ml of xylene. The mixture was cooled to 0° C and 20 grams of 2-octanone were added dropwise. Next, the reaction mixture was stirred for 17 hours at room temperature, 100 ml of water were added and the aqueous layer was separated from the organic layer. The aqueous phase was acidified with acetic acid. When it was cooled, an oil separated which crystallized after some time. Yield 9.8 g (35% selectivity, calculated on ethyl acrylate consumed, 34.6% selectivity, calculated on 2-octane consumed). Melting point 68°–70° C.

EXAMPLE 1

A mixture of 70 grams of sodium methylate and 250 ml of diethylene glycol dimethyl ether were introduced into a 1 liter four-necked flask provided with mechanical stirrer, dropping funnel, thermometer and reflux condenser. A mixture of 100 grams of ethyl acrylate and 256 grams of 2-octanone was added dropwise over a period of 3 hours. The temperature was maintained at 30° C, if necessary by cooling.

When the reaction was terminated the solution was acidified with 100 ml of concentrated hydrochloric acid to a pH of 3 and the sodium chloride formed was filtered off with suction. An analysis of the filtrate by gas-liquid chromatography indicated a content of 154.3 grams of 4-pentylcyclohexanedione-1,3 (84.8% selectivity, calculated on ethyl acrylate consumed and 87.5%, calculated on 2-octanone consumed). The solvent was removed from the filtrate under reduced pressure and the remaining product was recrystallized from ethyl ether/ethyl acetate. The 4-pentylcyclohexanedione-1,3 obtained in this manner had a melting point of 69°–70° C.

EXAMPLE 2

The reaction was carried out as described in Example 1, with the exception that the 2-octanone was first introduced into the flask together with the base and the solvent and the acrylate were added dropwise. Analysis of the reaction product indicated a content of 115.4 grams of 4-pentylcyclohexanedione-1,3 (63.4% selectivity, calculated on ethyl acrylate consumed and 67% selectivity calculated on 2-octanone consumed.

The conditions of comparative Example 1 and of Examples 1 and 2 are summarized in Table I.

EXAMPLES 3 to 14 and COMPARATIVE EXAMPLE 2

These examples were carried out as described in Example 1, but with the modifications specified in Table II.

EXAMPLE 15

A 1 liter four-necked flask, equipped with mechanical stirrer, dropping funnel, thermometer and reflux condenser was charged with a mixture of 70 grams of sodium methylate, 250 ml of diethylene glycol dimethyl ether and 86 grams of methyl arcylate. 144 Grams of methylethyl ketone were added dropwise over a period of 2 hours at −5° C.

When the reaction was terminated the reaction mixture was acidified to a pH of 3–4 and the sodium chloride formed was filtered off with suction. A gas-liquid chromatographic analysis of the filtrate indicated a content of 18 grams of 4-methylcyclohexanedione-1,3 (66% selectivity calculated on methyl acrylate consumed and 76.2% selectivity, calculated on methylethyl ketone consumed).

Referring to Tables I and II:

DEDME = diethylene glycol dimethyl ether
EA = ethyl acrylate
+) the 2-substituted derivative is formed in a 7.7% selectivity calculated on EA and 7.9% selectivity, calculated on 2-octanone;
++) besides the 4-substituted product, the 2-substituted derivative is formed in a 14.7% selectivity, calculated on EA and 15.6% selectivity, calculated on 2-octanone;
   con (A) and sel (A) means conversion and selectivity calculated on acrylate
   con (K) and sel (K) means conversion and selectivity calculated /on ketone.
DMF = dimethyl formamide
DEG = diethylene glycol diethyl ether
DME = monoethylene glycol dimethyl ether
MA = methyl acrylate
IPAC = isopropyl acrylate
DMSO = dimethyl sulfoxide

TABLE I

| Example | | solvent | | ketone $CH_3-\underset{\underset{O}{\|}}{C}-CH_2-C_5H_{11}$ | $\alpha,\beta$-unsaturated ester: ethyl acrylate | base NaOCH$_3$ | time hrs. | temperature °C |
|---|---|---|---|---|---|---|---|---|
| Comparative Example | 1 | Xylene | 200 ml | 20 g | 40 g | 16.2 g | 17.36 | 0 |
| Example | 1+) | DEDME | 250 ml | 256 g | 100 g | 70 g | 3.0 | 30 |
| Example | 2++) | DEDME | 250 ml | 256 g | 100 g | 70 g | 3.0 | 30 |

| | | Product 4-pentylcyclohexanedione-1,3 | | | |
|---|---|---|---|---|---|
| yield grams | con(A) wt. % | sel(A) mol % | con(A) wt. % | sel(A) mol % | |
| 9.8 | 39.0 | 35.0 | 100 | 34.6 | |
| 154.3 | 100 | 84.6 | 48 | 87.5 | |
| 115.4 | 100 | 63.4 | 47 | 67.0 | |

TABLE II

| Example | Solvent | | Ketone, $\underset{\underset{O}{\|}}{R_1CR_2}$ | | $\alpha,\beta$-unsaturated ester | | Base NaOCH$_3$ (g) | time hrs. | temperature (°C) |
|---|---|---|---|---|---|---|---|---|---|
| 3 | DEDME | 250 ml | $R_1=CH_3$ $R_2=C_2H_5$ | 144 g | MA | 86 g | 70 | 3.0 | 30 |
| 4 | DMF | 250 " | $R_1=CH_3$ $R_2=C_2H_5$ | 144 " | MA | 86 " | 70 | 3.0 | 30 |
| 5 | Dioxan | 250 " | $R_1=CH_3$ $R_2=C_2H_5$ | 144 " | IPAC | 114 " | 70 | 1.0 | 5 |
| 6 | DEDME | 250 " | $R_1=CH_3$ $R_2=C_2H_5$ | 144 " | IPAC | 114 " | 70 | 1.0 | 30 |
| 7 | DEG | 250 " | $R_1=CH_3$ $R_2=C_3H_7$ | 172 " | IPAC | 114 " | 70 | 3.0 | 6 |
| 8 | DEG | 250 " | $R_1=CH_3$ $R_2=C_7H_{15}$ | 142 " | MA | 86 " | 70 | 1.0 | 30 |
| 9 | DME | 350 " | $R_1CH_3$ $R_2=C_2H_5$ | 80 " | crotonic acid ethyl ester | 114 " | 70 | 1.0 | 40 |
| 10 | DMF | 400 " | $R_1=CH_3$ $R_2=CH_3$ | 53 " | IPAC | 86 g | 53 | 3.0 | 30 |
| Comp. Ex. 2 | xylene | 400 " | $R_1=CH_3$ $R_2=CH_3$ | 58 " | IPAC | 86 | 53 | 3.0 | 30 |
| 11 | DEDME + ethylacetate | 125 ml 125 ml | $R_1=CH_3$ $R_2=C_2H_5$ | 144 g | IPAC | 114 g | 70 g NaOCH$_3$ | 0.5 | 30 |

TABLE II-continued

| | | | | | | | | | |
|---|---|---|---|---|---|---|---|---|---|
| 12 | DMSO | 100 ml | $R_1=CH_3$ 58 g $R_2=C_2H_5$ | MA | 35 g | 30 g NaOCH$_3$ | 0.5 | 50 |
| 13 | DEDME | 100 ml | $R_1=CH_3$ 58 g $R_2=C_2H_5$ | MA | 35 g | 30 g Na-Amid | 1.0 | 40 |
| 14 | DEDME + DMF | 120 ml 120 ml | $R_1=CH_3$ 172 g $R_2=C_3H_7$ | MA | 86 g | 70 g NaOCH$_3$ | 2.0 | 30 |
| 15 | DEDME | 250 ml | $R_1=CH_3$ 144 g $R_2=C_2H_5$ | MA | 86 g | 70 g NaOCH$_3$ | 2.0 | −5 |

PRODUCT
4-R-cyclohexanedione-1,3*

| R | Yield (g) | con(A) wt. % | sel(A) mol % | con(K) wt. % | sel (K) mol % | Example No. |
|---|---|---|---|---|---|---|
| CH$_3$ | 88.3 | 100 | 70.4 | 43.1 | 81.3 | 3 |
| CH$_3$ | 96.9 | 100 | 76.1 | 47.9 | 80.1 | 4 |
| CH$_3$ | 82.3 | 100 | 65.3 | 43.4 | 75.1 | 5 |
| CH$_3$ | 84 | 90 | 74.0 | 43.2 | 77.1 | 6 |
| C$_2$H$_5$ | 92.7 | 97 | 68.6 | 42.0 | 79.1 | 7 |
| C$_6$H$_{13}$** | 104 | 100 | 52.9 | 100 | 52.9 | 8 |
| *** | 68.9 | 100 | 50.7 | 59.0 | 75.1 | 9 |
| H | 28 | 100 | 33.3 | 47.9 | 52.1 | 10 |
| H | — | — | — | — | — | Comp.Ex. 2 |
| CH$_3$ | 80 | 85.1 | 74.1 | 39 | 80.7 | 11 |
| CH$_3$ | 30 | 90.0 | 70.0 | 37 | 79 | 12 |
| CH$_3$ | 38 | 100 | 76 | 50 | 75 | 13 |
| C$_2$H$_5$ | 89 | 96 | 65.6 | 40 | 78.7 | 14 |
| CH$_3$ | 18 | 21.7 | 66 | 18.7 | 76.2 | 15 |

*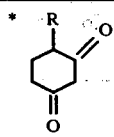

** besides the 4-substituted product, the 2-substituted product

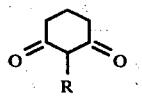 is formed in a yield of 27%, melting point 61–63° C acid number 290, structure defined by NMR and IR spectra

*** reaction product

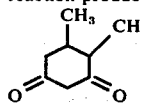 melting point 99–100° C

What is claimed is:
1. A process for the manufacture of a cyclohexandione-1,3 of the formula

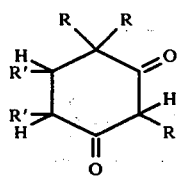

in which each of the radicals R, which may be identical or different, represents hydrogen, an alkyl group or an aryl group and the radicals R' represent hydrogen or an alkyl group, the cyclohexanedione-1,4 having up to 24 carbon atoms altogether, by reacting an α,β-unsaturated carboxylic acid ester of the formula

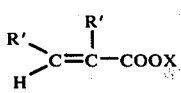

in which R' has the aforesaid meaning and X stands for an alkyl group, with a ketone of the formula

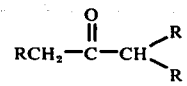

in which R has the aforesaid meaning, in the liquid phase in the presence of a strong base and of a solvent, which comprises using a solvent belonging to one of the following classes of compounds:
a. carboxylic acid amides of the formulae

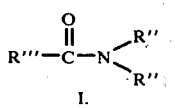 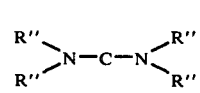

in which the radical R''' represents hydrogen or an alkyl group and the radicals R'', which may be identical or different, represent an alkyl or an aryl group and two of the radicals R'' bound to the same nitrogen atom or one of the radicals R'' and the radical R''' may form together a ring of methylene groups;
b. phosphoric acid amides of the formula

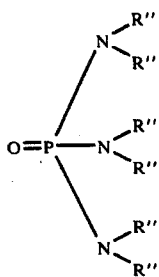

III.

in which the radicals R'' have the same meaning as in formulae I and II;

c. sulfoxides and sulfones of the formulae

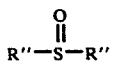 IV. 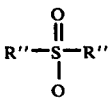 V.

in which the radicals R'' have the same meaning as in formulae I and II; and d. ethers of the formula

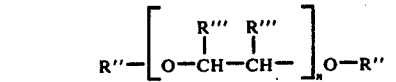

in which $n$ is in the range of from 1 to 5 and the radicals R''' and R'' have the same meaning as in formula I.

2. A process as claimed in claim 1, wherein the reaction is carried out at a temperature in the range of from $-10°$ to $+50°$ C.

3. A process as claimed in claim 1, wherein the reaction is carried out at a temperature in the range of from $0°$ to $100°$ C.

* * * * *